United States Patent [19]

Linna et al.

[11] Patent Number: 5,312,903
[45] Date of Patent: May 17, 1994

[54] LYSINE-GLYCOSYLATED RECOMBINANT INTERLEUKIN-2

[75] Inventors: Timo J. Linna, San Carlos, Calif.; Subramaniam Sabesan, Wilmington, Del.

[73] Assignee: E. I. du Pont de Nemours and Company, Wilmington, Del.

[21] Appl. No.: 531,970

[22] Filed: Jun. 1, 1990

[51] Int. Cl.$^5$ .............................................. C07K 13/00
[52] U.S. Cl. .................... 530/351; 530/395; 530/402; 530/405; 530/409; 424/85.2
[58] Field of Search ............... 530/351, 402, 405, 409, 530/395; 424/85.2

[56] References Cited

U.S. PATENT DOCUMENTS

| | | | |
|---|---|---|---|
| 4,904,584 | 2/1990 | Shaw | 530/351 |
| 5,153,310 | 10/1992 | Mitchell et al. | 530/351 |
| 5,217,881 | 6/1993 | Park | 530/351 |

FOREIGN PATENT DOCUMENTS

| | | |
|---|---|---|
| 0269455 | 7/1987 | European Pat. Off. |
| 8700056 | 1/1987 | World Int. Prop. O. |
| 9000565 | 1/1990 | World Int. Prop. O. |

OTHER PUBLICATIONS

Schwartz et al, *Arch. Biochem. Biophys* 181(2) 1977 pp. 542–549.
Parker et al, *FEBS Lett* 170(2) 1984, pp. 391–395.
G. Wilson, *J. Gen. Physiol.* 1979 v 74(4) pp. 495–509.
Van Brunt, Bio/Technology, Apr. 1986, pp. 835 and 839.
Inman et al., Immunochemistry 10 (1973) 165–174.
Stowell et al., Advances in Carbohydrate Chemisty and Biochemistry 37: 225–281 (1980).
Grimm et al, J. of Experimental Medicine 155: 1823–1841 (1982).
Mazunder et al., J. of Exp. Med 159: 495–507 (1984).
Grimm et al., Lymphokines, 9: 279–311 (1984).
Rosenberg et al., N. Eng. J. Med., 313: 1485–1492 (1985).
Rosenberg et al., N. Eng. J. Med., 316: 889–897 (1987).
Biochemistry & Molecular Biology, (1989) ed. G. D. Fasman, CRC Press Inc., 2000 Corp. Blvd. Boca Raton, FL 33431.
Schwartz et al., Adv. Carbohydr. Chem. Biochem., 40: 287–379 (1982).
Carbohydrate Biochem and Metabolism (1984) K. L. Roehrig AVI Publishing Co. Westport, Conn.
Conradt et al., Eur. J. Biochem., 153(2): 255–261 (1985).
Taniguchi et al., Nature, 302: 305–310 (1983).
Devos et al., Nucleic Acid Research, 11: 4307–4323 (1983).
Ju et al., J. Biol. Chem., 262: 5723–5731 (1987).
Katre et al. Proc. Natl. Acad Sci, USA 84: 1487–1491 (1987).
Conrad et al Eur J Biochem 153, 1985, pp. 255–261.
Lin et al., *J. Immunol* 141(11) 1988, pp. 3847–3851.
Goodson et al, *Bio/Technology* vol. 8, 1990, p. 343.

*Primary Examiner*—Garnette D. Draper

[57] ABSTRACT

This invention relates to chemical modification of biologically active proteins which alters the chemical, physical and biological properties of the proteins. More specifically, this invention relates to the additions of various carbohydrate moieties by chemical means to bacterially produced recombinant interleukin-2 molecules.

6 Claims, 3 Drawing Sheets

LYSINE-GLYCOSYLATED RECOMBINANT INTERLEUKIN-2

FIELD OF THE INVENTION

This invention relates to chemical modification of biologically active proteins which alters the chemical, physical and biological properties of the proteins. More specifically, this invention relates to the additions of various carbohydrate moieties by chemical means to bacterially produced recombinant interleukin-2 molecules.

BACKGROUND OF THE INVENTION

Some of the major advances in the area of carbohydrate chemistry are the development of methodologies to chemically synthesize complex oligosaccharides of defined sequences. The combination of the chemical and enzymatic syntheses of these materials affords greater possibilities to obtain oligosaccharides that cannot be made by means of chemical synthesis alone. Since there are commercially available monosaccharides, it is now possible to begin the synthesis of complex oligosaccharides with a starting sugar residue containing an appropriate tether and add many more complex sugars units as desired. Once the synthesis is completed, the oligosaccharide can be conveniently coupled via tethers to proteins. The methodology for synthesizing carbohydrate-tether conjugates has been described in U.S. Pat. No. 4,137,401. The general methodology for coupling ligands to proteins has been described by Inman et al., Immunochemistry 10, 165–174 (1973) and Stowell et al., Advances in Carbohydrate Chemistry and Biochemistry 37: 225–281, (1980).

Interleukin-2 (IL-2) is a protein secreted by lymphocytes which belongs to the class of immune modulating substances called lymphokines. IL-2 has been shown to modulate a number of immunological activities of lymphoid cells including cytotoxic T-cell activity, activation of natural killer (NK) cells, activation of B-cells, and generation of lymphokine activated killer (LAK) cells (cells that kill tumor cells but not normal cells). (Grimm et al., J Exp. Med., 155: 1823–1841 (1982); Mazumder et al., J. Exp. Med., 159: 495–507 (1984), Grimm et al., Lymphokines, 9:279–311 (1984)). Recently, treatment of cancer patients by administration of recombinant IL-2 (rIL-2) and autologous LAK cells has demonstrated the potential use of rIL-2 as an immunotherapeutic agent (Rosenberg et al., N. Eng. J. Med., 313: 1485–1492 (1985)). Rosenberg points out that in many patients, the administration of therapy was limited by the toxicity of rIL-2, and greater antitumor effects might occur if larger doses of rIL-2 and LAK cells could be administered. Rosenberg further teaches that rIL-2 can cause some of the side effects by possibly stimulating helper T cells to secrete other lymphokines, that may be toxic (Rosenberg et al., N. Eng. J. Med., 313:1485–1492 (1985)), Rosenberg et al., N. Eng. J. Med., 316:889–897 (1987).

Glycoproteins may be defined as "conjugated proteins containing as prosthetic group(s) one or more heterosaccharide(s), usually branched, with a relatively low number of sugar residues, lacking a serially repeating unit and bound covalently to the polypeptide chain." (Biochemistry and Molecular Biology, 1989, ed G.D. Fasman, CRC Press, Inc., 2000 Corporate Blvd., Boca Raton, Florida, 33431).

There are three classes of linkages between the carbohydrate and an amino acid of the protein portion in nature. One type has a N-glycosyl link to the amide nitrogen of asparnagine. A second type has a glycosidic bond between N-acetylgalactosamine and a serine or threonine hydroxyl, and a third has an attachment of the carbohydrate to the protein via the hydroxyl of hydroxylysine. (Carbohydrate Biochemistry and Metabolism, 1984, K. L. Roehrig, The AVI Publishing Company, Inc., Westport, Conn.).

Carbohydrates attached to proteins have been found to be essential in recognition or binding and to protect proteins against changes in temperature and pH (Schwartz et al., Adv. Carbohydr. Chem. Biochem., 40, 287–379 (1982)).

Natural IL-2 is a glycoprotein, with an estimated molecular weight of about 16,500 and contains carbohydrate O-linked to the threonine, the third amino acid from the amino terminal end (Conradt et al., Eur. J. Biochem., 153(2), 255–261 (1985). The gene responsible for the synthesis of human IL-2 has been cloned and sequenced (Taniguchi et al., Nature, 302: 305–310 (1983); Deves et al., Nucleic Acids Res., 11: 4307–4323 (1983)). The large quantities of IL-2 that are required for various clinical trials are currently produced as a result of cloning the gene for IL-2 and expressing it in $E.$ $coli$ (Ju et al., J. Biol. Chem., 262: 5723–5731 (1987). Even though the bacterially produced recombinant material lacks carbohydrates that are present on the natural material, it is functionally active. However, some of the physical properties of the bacterially produced material (rIL-2) are different from the native IL-2. The rIL-2 is produced as insoluble refractile bodies within the bacteria and therefore denaturants are required during its purification. In the absense of a detergent, purified rIL-2 has very limited solubility at neutral pH (Katre et al., Proc. Natl. Acad. Sci. USA, 84, 1487–1491 (1987). Due to rapid clearance, it also has a short circulatory serum half-life when administered to animals.

To delay the rate of in vivo clearance, EP 154,316 discloses chemically modified lymphokines, including rIL-2, containing polyethylene glycol bonded directly to at least one primary amino group of a lymphokine.

To overcome the limited solubility at neutral pH and the short circulatory half-life of rIL-2 purified from $E.$ $coli$, Katre et al. and WO87/00056 describe the modification of the rIL-2 by conjugating it with monomethoxy polyethylene glycol. The modified rIL-2 had enhanced solubility decreased plasma clearance and increased antitumor potency in a particular animal tumor model.

In this invention, various mono- and oligosaccharide-tether-conjugates have been attached by chemical means via an amide bond to the amino group of one or more of the 11 lysines in rIL-2, a biologically active protein. For the purposes of the disclosures of this invention, the process of attaching a saccharide(s) to at least one lysine in the rIL-2 molecule is considered glycolysation and the product is termed lysine-glycosylated rIL-2.

The glycoslated rIL-2 preparations of this invention were more readily soluble in water than unglycosylated IL-2 while retaining their biological activity. One biologically active glycosylated rIL-2 preparation was tested and found to be thermally more stable than rIL-2 when heated up to 90° C. Surprisingly, several glycosylated rIL-2 preparations which resulted from the method of this invention lost most of their T lymphocyte activating ability, while retaining most or all their biological activity, i.e., the ability to enhance NK cell and LAK cell activities.

SUMMARY OF THE INVENTION

There is provided by this invention a composition of matter comprising a lysine glycosylated rIL-2.

Further provided by this invention is a process for preparing a lysine-glycosylated rIL-2 comprising:

a) forming a carbohydrate-tetheracylhydrazide;

b) placing an aqueous solution of the carbohydrate-tether-acylhydrazide in reactive contact with an aqueous solution of rIL-2;

c) separating the lysine-glycosylated rIL-2.

Also provided by this invention is a process for preparing a lysine-glycosylated rIL-2 comprising:

(a) forming a carbohydrate-tetheracylhydrazide;

(b) placing the carbohydrate-tetheracylhydrazide dissolved in dimethyl formamide in reactive contact with a solution of rIL-2; and (c) separating the lysine-glycosylated rIL-2.

DETAILS OF THE INVENTION

Figure 1:
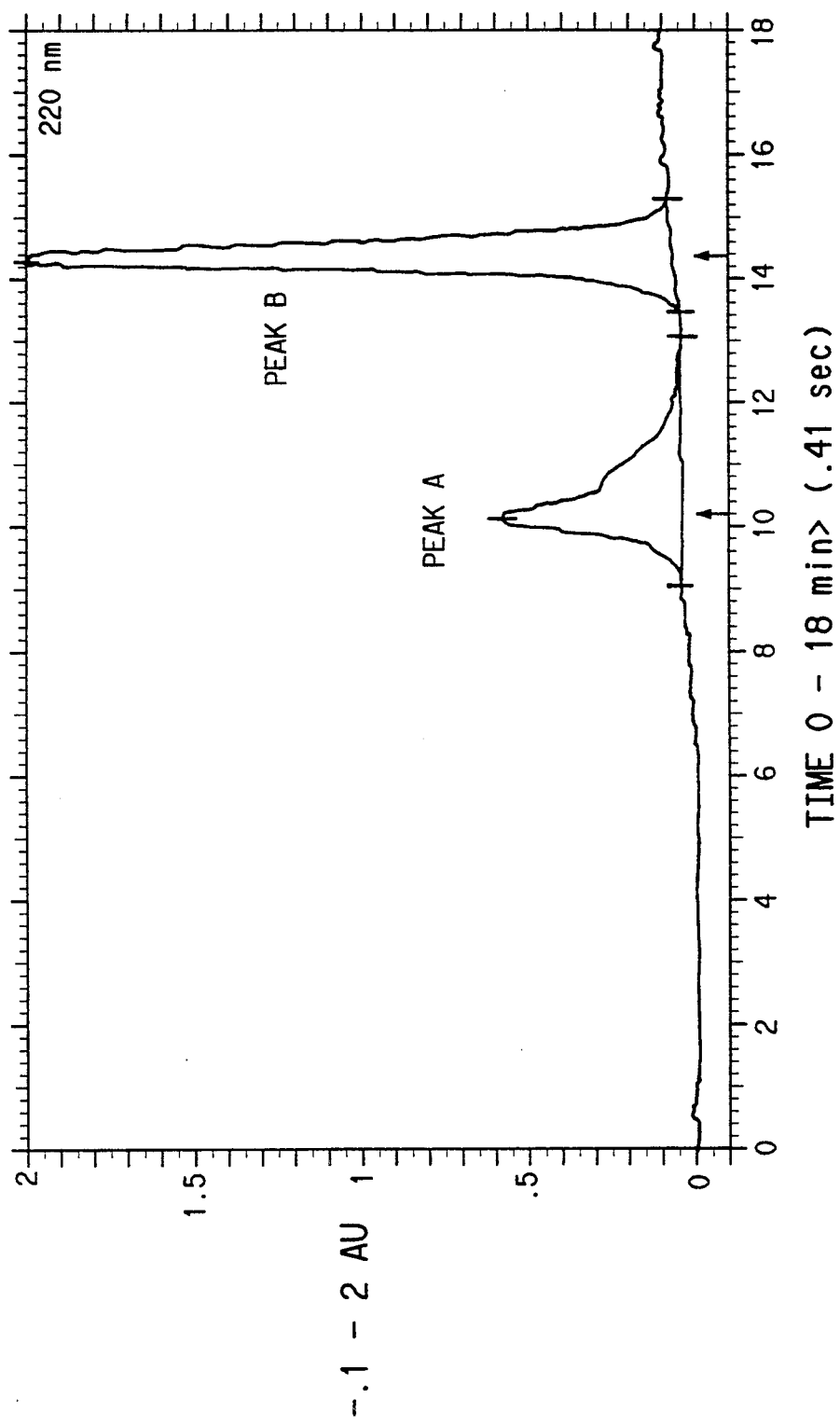
FIG. 1 shows the HPLC elution profile of βDGal(-1-3)βDGlcNAc-O-(CH$_2$)$_5$CONH-glycosylated rIL-2 of Example 4.

There is provided by this invention a composition of matter comprising a lysine-glycosylated recombinant interleukin-2 (rIL-2). The rIL-2 is glycosylated at at least one of the lysine residues in the rIL-2 molecule.

The term "recombinant interleukin-2", as used herein refers to a recombinant interleukin-2 as defined in WO87/00056. Briefly, such rIL-2 has comparable biological activity to native IL-2 prepared by recombinant DNA techniques as described, e.g., by Taniguchi et al., Nature, 302:305–310 (1983) and Devos, Nucleic Acids Research, 11:4307–4323 (1983). In general, the gene coding for IL-2 is excised from its native genome and inserted into a cloning vector to be cloned and then into an expression vector, which is used to transform a host organism, preferably a microorganism, and most preferably *E. Coli*. The host organism expresses the foreign gene to produce rIL-2 under expression conditions. Preferably the rIL-2 gene is human.

The carbohydrate to be linked to rIL-2 is conveniently selected from the group consisting of monosaccharides and oligosaccharides. More preferably, the oligosaccharides is nonimmunogenic and for convenience in preparation, comprises up to six monosaccharide residues. Examples of suitable monosaccharides and oligosaccharides are:

Compound
βDGal
βDGlcNAc
βDGal(1-3)βDGalNAc;
βDGal(1-3)βDGlcNAc;
βDGal(1-4)βDGlcNAc;
βDGlcNAc(1-6)βDGlcNAc;

-continued
Compound
βDGalNAc(1-4)βDGal(1-4)βDGlc;
βDGal(1-4)βDGlcNAc(1-6)βDGlcNAc;
βDGal(1-3)βDGalNAc(1-4)βDGal(1-4)βDGlc;
αDNeuAc(2-6)βDGal(1-4)βDGlcNAc(1-6)βDGlcNac;
and

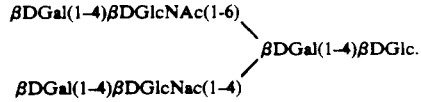

The carbohydrate-tether-acylhydrazide used in the processes of this invention can be prepared by attaching a carbohydrate such as those detailed herein, to a tether such as an ω-methoxycarbonylalkanol group as described in U.S. Pat. No. 4,137,401 which patent is incorporated by reference. Such a tether generally comprises a ω-carbonylalkoxy group of the general structure -O-(CH$_2$)$_n$CO- linked in a straight chain at the reducing end of the sugar followed by the remainder Of the sugar units. The result is a carbohydrate-tether conjugate of the general structure R-O-(CH$_2$)$_n$COOCH$_3$ (R = carbohydrate, O-(CH$_2$)$_n$CO = tether and n can generally be an integer in the range from about 4 to about 11.

Reacting carbohydrate-tether conjugates as described herein with hydrazine, converts the COOCH$_3$ in these structures to CONHNH$_2$. The reacted compound is referred to as the acylhydrazide. The mono- and oligosaccharides-tether-alcylhydrazides can then be coupled to the protein as shown below where R = the mono- or oligosaccharide:

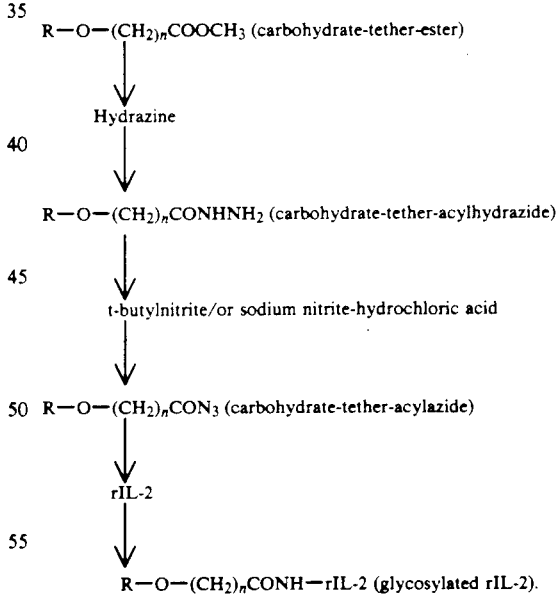

A novel process is provided for preparing a lysineglycosylated rIL-2, glycosylated at at least one lysine, by forming a mixture of carbohydrate-tether acylhydraside in water; placing the mixture in reactive contact with rIL-2 and separating the lysineglycosylated rIL-2. Preferably, the mixture additionally comprises dioxane, sodium nitrite or t-butylnitrite and hydrochloric acid to acidify the mixture. Such an aqueous process avoids the possibility of protein denaturing that can occur when the protein is exposed to organic solvents such as DMF.

Alternatively, a process is provided for preparing a lysine-glycosylated rIL-2 comprising forming a carbohydrate-tether-acylhydrazide, placing the carbohydrate-tether-acylhydrazide dissolved in dimethyl formamide in reactive contact with a solution of rIL-2 and separating the lysine-glycosylated rIL-2. Several lysine-glycosylated rIL-2 preparations (see Examples) made in DMF retained their biological activity while losing their T lymphocyte activating ability as defined herein.

The processes of this invention are also envisioned to encompass the step of enzymatically sialylating the glycosylated rIL-2.

The lysine-glycosylated rIL-2 of this invention was more soluble, as tested herein, than unglycosylated rIL-2 while surprisingly retaining its biological activity. Retention of biological activity is important for the rIL-2 to have in vivo therapeutic utility. Retention of biological activity as defined herein refers to lysine-glycosylated rIL-2 where NK and LAK activity, as measured herein, were shown to be at least 50%.

Surprisingly, several glycosylated rIL-2 preparations lost most of their T lymphocyte activating ability ($\leq 33\%$) while retaining their ability to enhance NK cell and LAK cell activities as defined above. Such preparations were made by the alternative processes, aqueous and DMF, of this invention. This differential activity of rIL-2 is expected to lead to a reduction of side effects, while maintaining antitumor effects in rIL-2 in vivo immunotherapy as discussed herein.

EXAMPLES

TEST METHODS

Procedures For Adding Carbohydrate-tetherconjugates To rIL-2

Procedure A:

Following standard procedure, mono- or oligosaccharide-tether-acylhydrazide is dissolved in anhydrous dimethyl formamide (DMF) and evaporated to dryness. Inmam et al., Immunochemistry, 10: 165–174 (1973) and Lemieux et al., Can. J. Biochem., 55: 507–512 (1978). This procedure is repeated twice. The syrupy material is then dissolved in DMF and cooled to $-20°$ C. A solution of hydrogen chloride in dioxane (4 M) is added followed by the addition of t-butyl nitrite. The solution is stirred at $-20°$ C. for 30 minutes. A solution of sulfamic acid in DMF is added and the solution is cooled to $-30°$ C. For addition to the rIL-2, the mono-or oligosaccharide acylhydrazide is dissolved at the desired concentration in DMF.

A solution of rIL-2 in 0.3 M mannitol or glucose (5.0 mL, 1.0 mg/mL) is lyophilized. The resulting powder is suspended in 5 mL of a buffer (pH 9.0) containing sodium borate (0.08 M) and potassium bicarbonate (0.35 M). The pH of the solution is then raised to 9.0 by the addition of 0.75 M potassium hydroxide.

The solution of rIL-2 is cooled in an ice bath with stirring and the solution of the mono- or oligosaccharide-tether-acylhydrazide is slowly added to it. The resulting solution is stirred in a cold room for 24 hours. The resulting glycosylated rIL-2 is recovered by means of high pressure liquid chromatography (HPLC).

Procedure B:

According to the process of this invention, the mono- or oligosaccharide-tether-acylhydrazide is dissolved in water maintained in an ice bath. Hydrochloric acid (4 M) in dioxane and sodium nitrite are added to acidify the mixture and the resulting mixture is stirred for 10 to 60 minutes. The mono- or oligosaccharide-tether-acylacylhydrazide solution is then added to r-IL2 solution prepared as in procedure A and the resulting solution is stirred in an ice bath for 24 hours. The resulting glycosylated rIL-2 is then recovered by means of HPLC.

Procedure For Recovery and Purification Of Lysine-Glycosylated rIL-2

Purifications of the lysine-glycosylated rIL-2 were done using a Vydac C-4 column ((The Nest Group, Southboro, MA), 4.6 mm X 15 cm, 5 micron particle size, 300 Å pore size) Estimations of protein concentration are done using the same column material but a shorter column (i.e., 4.6 mm X 5 cm). HPLC grade water, acetonitrile and trifluroacetic acid (Pierce Chemical Co., Rockford, IL) are used. The proportion of water-acetonitrile-trifluoracetic acid in solvent A is 85:15:0.1, while in solvent B the ratio is 10:90:0.1. A Waters HPLC system (Waters, Milford, MA) equipped with a 600E pump, Wisp autoinjector, Rheodyne 7125 manual injector (Altech Associates, Deerfield, IL) and 990 photodiode array detector (Waters, Milford, MA) was used. The glycosylation reaction mixture is loaded on to the reverse phase column (typically 1.5 to 2 mg of protein was loaded) and washed (normally 2 min) with solvent A to remove all the UV active materials. The composition of the eluting fluid is then gradually changed, during a period of 5.5 min, to contain 45% of solvent B and then maintained for about 2 min of additional elution wherein all the aggregated protein impurities elutes. Following this, the amount of solvent B is increased until the eluting fluid contained only solvent B and the elution is carried out for a period of 2.5 min. Glycosylated rIL-2 elutes as a single peak at this eluant composition (see e.g., FIG. 1). The product is collected in 17×100 cm sterile polypropylene tubes, frozen and lyophilized. Finally, the glycosylated rIL-2 is dissolved in 0.3 M glucose solution and stored at $-78°$ C. The concentration of protein is estimated by comparing the absorptions of standard rIL-2 and the glycosylated rIL-2 at 280 nm.

Determination of the Increased Solubility of Glycosylated rIL-2

The increased solubility of glycosylated IL-2 over that of unglycosylated rIL-2 was determined by visually comparing the ease of dissolution of 1 mg of the glycosylated rIL-2 with that of the unglycosylated rIL-2 in aqueous buffers and in the absence of any detergent. In all Examples, the fluid in the tubes to which the glycosylated IL-2 was added, rapidly became clear and there was no discernable residue in the bottom of the tube on standing. In contrast, the solution containing unglycosylated rIL-2 had noticeable residue in the bottom of the tube and was not completely clear when agitated.

Determination of Increased Stability of Glycosylated rIL-2

Figure 2:
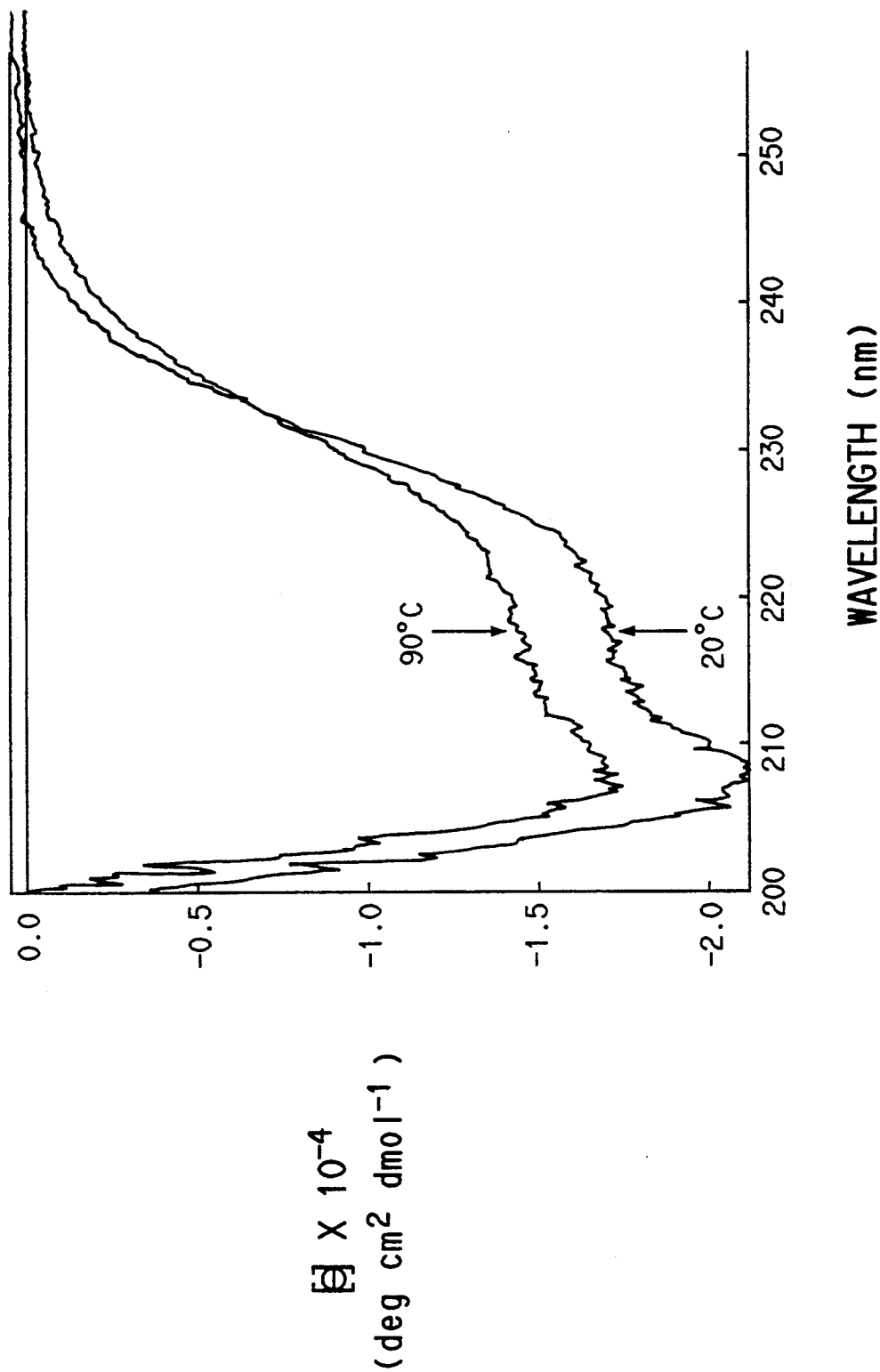
FIG. 2 is a graph showing the circular dichroism profile of glycosylated rIL-2 at 20° C. and at 90° C., Example 7, Sample 30-2.

The increased stability of the glycosylated rIL-2 (Example 7, Sample 30-2) relative to unglycosylated rIL-2 was established by circular dichroism measurements at room temperature as well as at 90° C. (FIG. 2).

Enhancement of Natural Killer (NK) Cell Activity

Circulating normal lymphocytes exhibit the ability to kill certain cultured tumor cell lines (Herberman et al., Science, 214: 24 (1981). This ability is markedly enhanced following prior incubation with IL-2. (Trinchieri et al., J. Exp. Med., 160: 1147-1169 (1984).

Non-adherent human peripheral blood lymphocytes were obtained after Ficoll-Hypaque centrifugation and plastic adherence, using procedures described by Boyum, Scand. J. Clin. Lab. Invest., 2I (Suppl. 97) 77-89 (1968). These lymphocytes were used as effector cells in a short-term (3.5 h) $^{51}$[Cr] release assay against K562 erythroleukemia target cells (ATCC accession number CCL-243) which had been labeled with chromium $^{51}$[Cr], using procedures described by Linna et al., J. Immunol., 120:1544-1549 (1978). Effector cells were added to target cells at ratios of 60, 20, 6.6, and 2.2. The number of target cells required to release 50 percent of the 51[Cr] was determined for each rIL-2 or glycosylated rIL-2 preparation when the effector cells were incubated with 5 units. By comparing the number of effector cells required to bring about 50 percent lysis when the effector cells were stimulated with rIL-2 and those stimulated with glycosylated rIL-2, their relative activities were determined. The activity of the glycolsylated rIL-2 is reported as the percent of that of the equivalent amount of unglycosylated rIL-2.

Preparations of effector cells were incubated for 3 days in the presence of the different preparations of glycosylated rIL-2, and unglycosylated rIL2 of known potency. The concentrations were adjusted so that effector cells were incubated with 5 units of rIL-2 and an equivalent of 10, 5, 2, and 1 of these rIL-2 units of glycosylated rIL-2. The equivalent units of glycosylated rIL-2 were determined by knowing the specific activity of the rIL-2 prior to its glycosylation and assuming no loss of activity during glycosylation.

Generation of Lymphokine-Activated Killer (LAK) Cell Activity in Human Peripheral Blood Lymphocytes The procedure to generate LAK cell activity from preparations of human peripheral lymphocytes is the same as that used to enhance NK cell activity. The assay for LAK cell activity is done like the assay for NK cell activity except that the target cells are Raji cells. Raji cells can be obtained from the American Type Culture Collection, Rockville, MD 20852, bearing ATCC accession Number CCL-86. Raji cells are from a lymphocyte tumor cell line originally derived from a patient with Burkitt's lymphoma. They are not lysed by NK cells. Assay results were determined as they were for the NK cells and the activity of the glycosylated rIL-2 is reported as the percent of that of the equivalent amount of unglycosylated rIL-2.

Assay for the Stimulation of Lymphocyte Proliferation by rIL-2

The stimulation of lymphocyte proliferation by rIL-2 was determined by measuring the IL-2 concentration-dependent incorporation of $^3$H-thymidine by a cloned, IL-2 dependent murine cell line as described by Gillis et al., J. Immunol. 120:2027-2032 (1978). Comparison of the incorporation induced by an unknown sample with that of a laboratory standard yields the relative bioactivity of the sample. The laboratory standard contains 34 BRMP units/ml (units defined by the Biological Response Modifiers Program, National Institutes of Health, Bethesda, MD).

The assay begins by adding 100 μL of eight two-fold dilutions (in assay media which is Iscoves DMEM (a modification of Dulbecco's modified Eagle's Medium), 15% fetal calf serum, 2 mM glutamine, 1 mM sodium pyruvate, $5 \times 10^{-5}$ M 2-mercaptoethanol, 0.05 μg/mL gentamicin) of the standard and unknown samples to separate wells of a well microtiter plate.

Two additional wells receive 100 μL of assay medium as background controls. Before initiating the serial two-fold dilution, all unknown samples are diluted to approximately 34 BRMP units per mL according to estimated activity. Then 100 μL of a washed suspension of IL-2 dependent murine tumor-specific cytotoxic T-lymphocytes at a concentration of $4 \times 10^4$ cells/mL in assay medium is added to each well (4000 cells/well). The plate is incubated overnight at 37° C. (5% CO$_2$, 95% humidity) and 50 μL of $^3$H-thymidine deoxyriboside with specific activity 6.7 ci/mmole at 10 μci/mL concentration is added to each microplate well. The plate is incubated at 37° C. for an additional 4 h. The cells are harvested on glass fiber filter paper using the PHD ™ cell harvester and the level of $^3$H radioisotope on each filter disk is determined.

To standardize the data, the incorporation of radioisotope of each concentration of a sample is compared to the maximum incorporation achieved with the IL-2 standard. The values which are generated are calculated using weighted linear regression through least squares analysis; wherein each data point is weighed according to an appropriate measure of accuracy. The fitted lines generated for both the standard and unknown samples are forced to be parallel prior to calculating the units of rIL-2 activity. The units of rIL-2 activity are calculated from the distance of the log$_2$ dilution axis between the parallel lines. Because the values of glycosylated rIL-2 samples are compared to a standard and non-glycosylated rIL-2 samples and because the assay is not absolutely precise, values of some of the samples of glycosylated rIL-2 give values greater than the non-glycosylated samples, i.e., greater than 100%.

EXAMPLE 1

Synthesis of βDGal-O-(CH$_2$)$_5$CONHNH$_2$ and the Properties of rIL-2 Conjugated with it Synthesis of βDGal-O-(CH$_2$)$_5$CONHNH$_2$ A solution of acetobromogalactose (38.4 g) in 200 mL of dry dichloromethane was added over a period of 60 min to a vigorously stirred suspension containing 5-methoxycarbonylpentanol (30.0 g), anhydrous silver carbonate (31.7 g, Aldrich, Milwaukee, WI), 3 angstrom molecular sieves (30.0 g) and anhydrous calcium sulphate (20.0 g) in dry dichloromethane (350 mL). After 20 h, the solution was filtered over a celite pad and then evaporated to dryness. The syrup was dissolved in pyridine (75 mL) containing acetic anhydride (50 mL) and 4-N,N-dimethylaminopyridine (10 mg) and stirred at room temperature for 3 h. The reaction mixture was then poured over crushed ice (200 g) and the product was extracted with dichloromethane (2 × 200 mL). The combined dichloromethane layer was washed with ice cold 1 M hydrochloric acid and this procedure was repeated till the aqueous layer was acidic. Finally, the dichloromethane layer was washed with saturated sodium bicarbonate solution, dried over anhydrous magnesium sulphate and evaporated. To the crude syrup, n-hexane was added (200 mL), shaken well and the hexane layer was decanted. This procedure was repeated three times. Finally, the syrup was dissolved in anhydrous methanol (300 mL). Sodium methoxide solution (15 mL of 0.5 M solution) was added to the syrup and this mixture was stirred at room temperature for 3 h. The reaction mixture was neutralized with IR-120 H resin, filtered and evaporated to a dry residue (26.1 g).

The above residue (229 mg) was dissolved in methanol (15 mL). Anhydrous hydrazine (5 mL) was added to this and the mixture was refluxed for 3 h. The solution was evaporated to dryness. The residue was dissolved in 5 mL of deionized water and applied on a column (60 cm × 4 cm) of Bio gel P-2 (Bio Rad, Cambridge, MA 02139) (200–400 mesh) equilibrated and eluted with water. Fractions (8 mL) were collected and assayed for the product by thin layer chromatography (TLC) using ethylacetate-ethanol-water (8:4:1) as the TLC eluant. The product containing fractions were pooled and lyophilized to get a colorless powder (195 mg). The structural identity was confirmed by $^1$H nmr.

Preparation of βDGal-tether-rIL-2 by Procedure A

βDGal-O-(CH$_2$)$_5$CONHNH$_2$ (8.18 mg) was reacted with a solution of dimethyl formamide (1.86 mL) containing t-butyl nitrite (5.0 μL) and 4 M hydrochloric acid in dioxane (40 μL) and then treated with sulfamic acid (0.97 mg in 20.5 μL of DMF). The resulting solution was reacted with a rIL-2 (12.5 mg) solution as described in Procedure A. The ratio of the monosaccharide to rIL-2 was 0.65 to 1 by weight. The weight of the HPLC purified glycosylated protein recovered was 4.34 mg.

rIL-2 glycosylated with βDGal-O-(CH$_2$)$_5$CONHNH$_2$ was tested for its solubility, its ability to enhance NK cell activity, generate LAK activity, and stimulate lymphocyte proliferation.

Results:

Solubility: The recovered glycosylated rIL-2 was significantly more soluble than native rIL-2.

| NK enhancing activity: | 104% |
| --- | --- |
| LAK generating activity: | 111% |
| Ability to stimulate the proliferation of lymphocytes: | 45% |

Preparation of βDGal-tether-rIL-2 by Procedure B

βDGal-O-(CH$_2$)$_5$CONHNH$_2$ (8.50 mg) was reacted with an aqueous solution (1 mL) of sodium nitrite and 4 M hydrochloric acid in dioxane (40 μL) and then with a rIL-2 (12.5 mg) solution as described in Procedure B. The ratio of the monosaccharide to rIL-2 was 0.68 to 1 by weight. The amount of glycosylated rIL-2 recovered by HPLC was 4.37 mg.

rIL-2, glycosylated in this manner with βDGal-O-(CH$_2$)$_5$CONHNH$_2$, was tested for its solubility, its ability to enhance NK cell activity, generate LAK activity, and stimulate lymphocyte proliferation.

Results:

Solubility: The recovered glycosylated rIL-2 was significantly more soluble than native rIL-2.

| NK enhancing activity: | 104% |
| --- | --- |
| LAK generating activity: | 99% |
| Ability to stimulate the proliferation of lymphocytes: | 40% |

EXAMPLE 2

Synthesis of βDGlcNAc-O-(CH$_2$)$_5$CONHNH$_2$ and the Properties of rIL-2 Conjugated with it The methyl ester namely, the βDGlcNAc-O-(CH$_2$)$_5$COOCH$_3$ was made according to the method of Lemieux et al., J. Am. Chem. Soc., 97: 4076–4083 (1975), except for the use of 5-methoxycarbonylpentanol for 8-ethoxycarbonyloctanol. The ester (523 mg) was converted to the hydrazide βDGlcNAc-O(CH$_2$)$_5$CONHNH$_2$ by refluxing in methanol containing hydrazine as described in Example 1. Yield 452 mg.

βDGlcNAc-O-(CH$_2$)$_5$CONHNH$_2$ (8.82 mg) was reacted with a solution of dimethyl formamide (1.05 mL) (Procedure A) containing t-butyl nitrite (4.5 μL) and 4 M hydrochloric acid in dioxane (26 μL), then treated with sulfamic acid (0.97 mg in 20 μL of DMF) and reacted with a rIL-2 solution (5 mL, 1 mg/mL) as described in Procedure A. The product was dialysed against water for 24 hours prior to purification by HPLC. The ratio of monosaccharide to rIL-2 was 1.76 to 1 by weight. The weight of the HPLC recovered protein was 2.52 mg.

βDGlcNAc-O-(CH$_2$)$_5$CONHNH$_2$ conjugated with rIL-2 was tested for its solubility, its ability to enhance NK cell activity, generate LAK cell activity, and stimulate lymphocyte proliferation.

Solubility: significantly more soluble than native rIL-2.

| NK enhancing activity: | 13% |
| --- | --- |
| LAK generating activity: | 0% |
| Ability to stimulate the proliferation of lymphocytes: | 4% |

EXAMPLE 3

Synthesis of βDGal(1-3)βDGalNAc-O-(CH$_2$)$_5$CONHNH$_2$ and the Properties of the rIL-2 Conjugated with it The methyl ester namely βDGal(1-3)βDGalNAc-O-(CH$_2$)$_5$COOCH$_3$ was made according to the published procedure of Sabesan et al., J. Am. Chem. Soc., 108:2068 (1986). The ester (120 mg) was then converted to the hydrazide as described in Example 1. The weight of the product was 106 mg..

βDGal(1-3)βDGalNAc-O(CH$_2$)$_5$CONHNH$_2$ (13.0 mg) was reacted with 1.5 mL of DMF (Procedure A) containing 26 μL of 4 M hydrochloric acid in dioxane and t-butyl nitrite (4.5 μL) followed by reacting with sulfamic acid (0.97 mg in 20 μL DMF) and rIL-2 solution (5 mL, 1 mg/mL) as described in Procedure A. The ratio of the disaccharide to the rIL-2 was 2.6 to 1 by weight. The weight of the HPLC purified product was 2.61 mg.

βDGal(1-3)βDGalNAc-O-(CH$_2$)$_5$CONHNH$_2$ conjugated with rIL-2 was tested for its solubility, its ability to enhance NK cell activity, generate LAK cell activity, and stimulate lymphocyte proliferation.

Results:

Solubility: readily soluble in an aqueous solution

| | |
|---|---|
| NK enhancing activity: | 21% |
| LAK generating activity: | 21% |
| Ability to stimulate the proliferation of lymphocytes: | 5% |

EXAMPLE 4

Synthesis
βDGal(1-3)βDGlcNAc-O(CH$_2$)$_5$CONHNH$_2$ and the Properties of rIL-2 Conjugated with it First the methyl ester βDGal(1-3)βDGlcNAc-O-(CH$_2$)$_5$COOCH$_3$ was prepared according to the method of Lemieux et al., J. Am. Chem. Soc., 97: 4076–4083 (1975), except for the use of 5-methoxycarbonylpentanol in making the intermediate βDGlcNAc-O-(CH$_2$)$_5$COOCH$_3$. Also, sodium methoxide in methanol was used in the de-O-acetylation of the final product. This methyl ester was converted to the hydrazide as described in Example 1.

Conjugation to rIL-2

Procedure A:

βDGal(1-3)βDGlcNAc-O-(CH$_2$)$_5$COOCH$_3$ (13.0 mg) was reacted with 1.5 mL of DMF containing 26 μL of 4 M hydrochloric acid in dioxane and t-butyl nitrite (4.5 μL) followed by reacting with sulfamic acid (0.97 mg in 20 μL of DMF) and rIL-2 solution (5 mL, 1 mg/mL) as described in Procedure A. The ratio of oligosaccharide to rIL-2 was 2.6 to 1 by weight. The weight of the HPLC purified product was 2.94 mg.

Results:

Solubility: readily soluble in an aqueous solution.

| | |
|---|---|
| NK enhancing activity: | 24% |
| LAK generating activity: | 28% |
| Ability to stimulate the proliferation of lymphocytes: | 6% |

Procedure B:

Two sets of reactions were carried out (sample 117-1 and 117-2) according to Procedure B to demonstrate the process of this invention.

βDGal(1-3)βDGlcNAc-O-(CH$_2$)$_5$CONHNH$_2$ (39.0 mg) was dissolved in 1 mL of water and cooled in an ice bath. A solution of hydrochloric acid (4 M) in dioxane (600 uL) and a solution of aqueous sodium nitrite (450 mM, 250 μL) were added and the solution was stirred for 30 min. This was then followed by the addition of a solution of sulfamic acid in water (250 μL of a stock solution prepared by dissolving 14.4 mg of acid in 1 mL water) and the azide solution was stirred in an ice bath.

Two solutions, each containing 5.8 mg of rIL-2 in sodium borate buffer (see Procedure A) were prepared, labeled 117-1 and 117-2, then treated with 700 μL and 1400 μL of the above azide solution, respectively, and stirred in a cold room. The resulting glycosylated rIL-2 was obtained according to Procedure A. The ratios of oligosaccharide to rIL-2 were 2.3:1 and 4.6:1 by weight respectively. The yields were: 117-1 = 2.06 mg; 117-2 = 1.64 mg.

Results:

117--1
Solubility: readily soluble in an aqueous solution.

| | |
|---|---|
| NK enhancing activity: | 81% |
| LAK generating activity: | 86% |
| Ability to stimulate the proliferation of lymphocytes: | 15% |

117-2
Solubility: readily soluble in an aqueous solution.

| | |
|---|---|
| NK enhancing activity: | 73% |
| LAK generating activity: | 67% |
| Ability to stimulate the proliferation of lymphocytes: | 11% |

EXAMPLE 5

Synthesis βDGlcNAc-O-(CH$_2$)$_5$CONHNH$_2$ and the Properties of rIL-2 Conjugated with it A solution of βDGlcNAc-O-(CH$_2$)$_5$COOCH$_3$ (123 mg) and uridine-5'-diphospho-galactose (UDP-Galacose, Sigma Chemical Co., St. Louis, MO 63178) (100 mg) in 10 mL of a buffer containing manganese chloride (1 mM), sodium cacodylate (pH 7.0, 1 mM), galactosyltransferase (EC 2.4.1.22, 12.5 U) and bovine serum albumin (10 mg) were incubated at 37° C. for 20 h. The reaction mixture was diluted to 30 mL and eluted through a column (1.5 cm × 8 cm) of Dowex 1×2 (Cl-form, 200–400 mesh) with water (200 mL). The solution was evaporated to dryness, redissolved in 5 mL of water and applied on a column (60×4 cm) of Bio Gel P-2 (200–400 mesh, Bio Rad, Cambridge, MA 02139). Equilibrations followed by elutions with water afforded two pools; one containing the pure disaccharide (pool 1) and the other with the disaccharide and the monosaccharide (pool 2). Evaporation of the water afforded colourless materials: 46 mg from pool 1 and 94.5 mg from pool 2. The identity of the product from pool 1 was established as βDGal(1-4)βDGlcNAc-O-(CH$_2$)$_5$COOCH$_3$ based on the $^1$H nmr. The residue from pool 1 (42.0 mg) was converted to the hydrazide as described in Example 1. Yield 23 mg.

βDGal(1-4)βDGlcNAc-O-(CH$_2$)$_5$CONHNH$_2$ (15.3 mg) was reacted with 1.5 mL of DMF (Procedure A) containing 29 μL of 4 M hydrochloric acid in dioxane and t-butyl nitrite (4.5 μL) followed by reacting with sulfamic acid (0.97 mg in 20 μL of DMF) and a rIL-2 (6.0 mg) solution as described in Procedure A. The ratio of oligosaccharide to rIL-2 was 2.6 to 1 by weight. The reaction mixture was dialyzed against deionized water and then purified by HPLC. The weight of the HPLC purified product was 3.45 mg.

βDGal(1-4)βDGlcNAc-O-(CH$_2$)$_5$CONHNH$_2$ conjugated with rIL-2 was tested for its solubility, its ability to enhance NK cell activity, generate LAK cell activity, and stimulate lymphocyte proliferation.

Results:

Solubility: readily soluble in an aqueous solution.

| | |
|---|---|
| NK enhancing activity: | 92% |
| LAK generating activity: | 64% |
| Ability to stimulate the | 7% | proliferation of lymphocytes:

EXAMPLE 6

Synthesis of
βDGlcNAc(1-6)βDGlcNAc-O-(CH$_2$)$_5$CONHNH$_2$
and the Properties of rIL-2 Conjugated with it βDGlcNAc(1-6)βDGlcNAc-O-(CH$_2$)$_5$CONHNH$_2$
was prepared as outlined in Scheme 1.

chloride solution. It was dried over anhydrous magnesium sulfate and evaporated to a dry residue which was redissolved in a mixture of pyridine (80.8 mL) and acetic anhydride (47.2 mL). After being stirred at room temperature for 18 h, the reaction mixture was poured over ice and the product was extracted with dichloromethane (3×100 mL). The combined organic extracts were washed with ice cold 1M hydrochloric acid (till the aqueous layer was acidic), water and saturated sodium bicarbonate solution. After drying over anhydrous magnesium sulfate, the solvent was evaporated Scheme 1

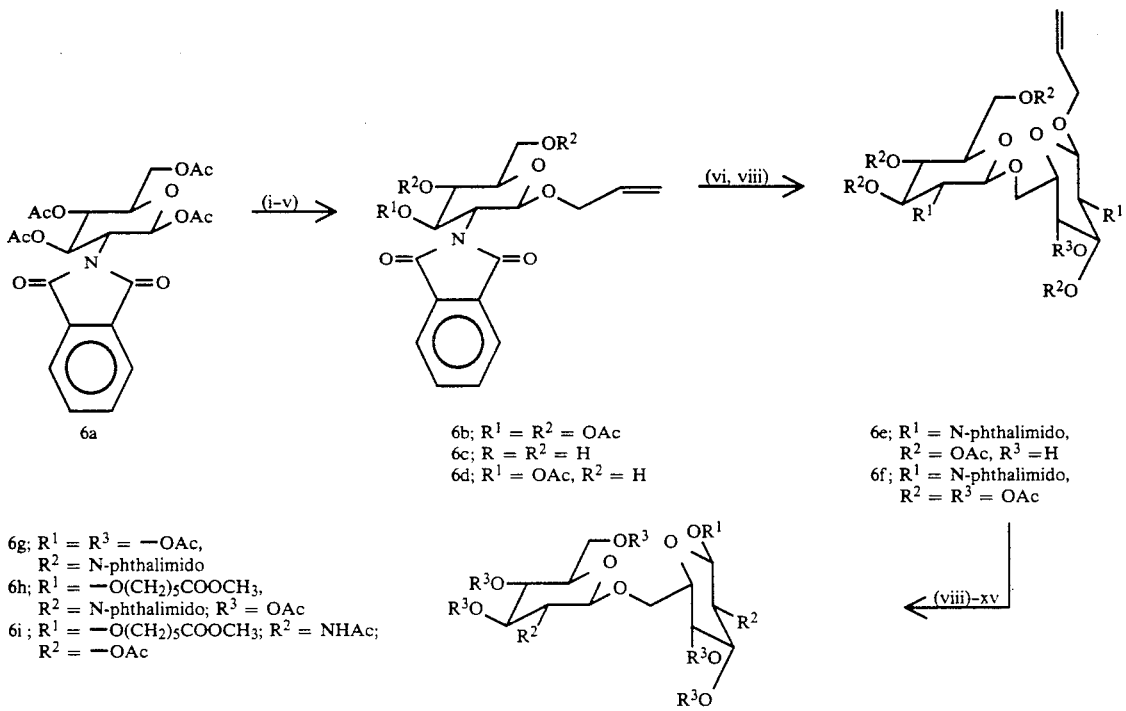

A solution of 2-deoxy-2-phthalimido-1,3,4,6-tetra-O-acetyl-β-D-glucopyranose (6a of Scheme 1) (47.7 g) in 1,2-dichloroethane (250 mL) was slowly added to allyloxytrimethyl silane (Aldrich, 20.2 mL), then, trimethylsilyl trifluoromethanesulfonate (Aldrich, 19.3 mL) was added dropwise. The reaction mixture was stirred at room temperature under a nitrogen atmosphere for 18 h, cooled to 0° C. and diluted with 200 mL of dichloromethane. The organic layer was separated, washed with ice cold water and saturated sodium bicarbonate, dried over anhydrous magnesium sulfate and evaporated to afford a solid (44.12 g). The structure of this product as 6b (of Scheme 1) was established on the basis of $^1$H nmr. Crude 6b (44.0 g) was stirred in 505 mL of methanol containing sodium methoxide (9.0 mM) for 4 h. It was then neutralized with IR-120 H$^+$ resin, filtered and evaporated to a dry residue (31.06 g). The structure of this product was established as 6c (of Scheme 1) based on $^1$H nmr. The product 6c (29.66 g) was suspended in acetonitrile (300 mL) containing benzaldehyde dimethylacetal (Aldrich, 30 mL) and p-toluenesulphonic acid (500 mg). The mixture was stirred at room temperature for 18 h. The material was then poured over ice and the product was extracted with ethylacetate (500 mL). The ethylactate layer was washed with saturated sodium bicarbonate and sodium and the residue was heated with 50 percent aqueous acetic acid at 100° C. for 30 min. The reaction mixture was cooled and diluted with ice cold water (300 mL). The product was extracted with ethyl acetate (3×200 mL) and the ethyl acetate extracts were combined and washed with saturated sodium bicarbonate. After drying, the solvent was evaporated and the residue was washed with ice cold dichloromethane to yield pure 6d (of Scheme 1, 17.0 g). Evaporation of the washings and further purification of the residue by silica gel chromatography afforded another 5.26 g of pure 6d. The structure of 6d was firmly established on the basis of 1H nmr. The residue 6d (15.64 g) was dissolved in anhydrous nitromethane (200 mL) containing silver trifluoromethane sulfonate (11.28 g) and s-collidine (5.28 mL). The solution was cooled to −28° C. and stirred under a nitrogen atmosphere. A solution of 2-deoxy-2-phthalimido-3,4,6-tri-O-actyl-α-D-glucopyranosyl bromide (21.92 g) in nitromethane (200 mL) was added over a period of 10 min and the reaction mixture was stirred at ambient temperature for 2 h. The reaction mixture was diluted with ethyl acetate filtered through a pad of celite. The filtrate was washed with 5 percent sodium thiosulfate solution, 1 M hydrochloric acid and then with saturated sodium bicarbonate solution. The product 6e (of Scheme 1) was purified by silica gel chromatography. Yield 13.0 g. Compound 6e (12.06 g) was acetylated with pyridine (40 mL) and acetic anhydride (7 mL). The reaction mixture was then poured over ice, extracted with dichloromethane and the organic layer was washed with 1 M hydrochloric acid and saturated sodium bicarbonate. After evaporation of the solvent, 6f (of Scheme 1) was obtained as a colorless material (12.6 g). Product 6f (9.36 g) was dissolved in dry tetrahydrofuran (180 mL) containing bis(diphenyl methyl phosphinyl)1,4-cyclooctadienyl irridium(I) phosphorous hexafluoride (110 mg). The solution was gently evacuated, then equilibrated with dry nitrogen. This procedure was repeated twice and the solution was exposed to a hydrogen atmosphere for 2 min. The color of the reaction mixture changed from red to pale orange. At this time, the system was gently evacuated and equilibrated with nitrogen and stirred at room temperature for 3 h. The solution was evaporated to dryness. The residue was dissolved in a solution containing acetone (270 mL), water (30 mL), mercuric chloride (30 g) and yellow mercuric oxide (150 mg) and stirred for 90 min. Most of the acetone was evaporated and the residue was taken up in 300 mL of dichloromethane. The organic layer was washed with 10% potassium iodide solution (3×100 mL), water and saturated sodium bicarbonate solution. After being dried over anhydrous magnesium sulfate, the solution was evaporated to a dry residue (9.07 g). The above residue (1.621 g) was dissolved in a mixture of pyridine (4 mL)-acetic anhydride (0.94 mL) containing 25 mg of N,N-dimethylaminopyridine (DMAP) and stirred for 6 h. The product from this reaction mixture was worked up as described for 6f (of Scheme 1) to afford a colorless residue (1.495 gm). The structure was established as 6g (of Scheme 1) by $^1$H nmr. A solution of 6g (853 mg) in 1,2-dichloroethane (5 mL) containing 4 angstrom molecular sieves (200 mg), $(CH_3)_3SiO(CH_2)_5COOCH_3$ (0.29 mL) and trimethylsilyl trifluoromethanesulfonate (0.21 mL) was stirred at room temperature for 5 h. It was then worked up as described above for compound 6a. Final purification by silica gel chromatography afforded 6h (of Scheme 1) as a colorless foam (.788 mg). The compound 6h (598 mg) was dissolved in 30 mL of methanol containing 0.2 mL of 0.5 M sodium methoxide and stirred at room temperature for 3 h. It was neutralised with IR-120 H+ resin and the solvent was evaporated to obtain a dry residue (462 mg). This was then dissolved in methanol containing anhydrous hydrazine and refluxed for 19 h. The reaction mixture was evaporated to dryness and the residue was dissolved in pyridine-acetic anhydride mixture containing DMAP (10 mg) and stirred at room temperature for 18 h. It was then worked up as described for 6f. After silica gel chromatography, the product 6i (of Scheme 1) was obtained as a colorless residue. This was then deacetylatd as described above with sodium methoxide in methanol to yield the methyl ester $\beta DGlcNAc(1-6)\beta DGlcNAc-O-(CH_2)_5COOCH_3$. This (551 mg) was then converted to the acylhydrazide $\beta DGlcNAc(1-6)\beta DGlcNAc-O-(CH_2)_5CONHNH_2$ as described in Example 1. Yield (470 mg).

$\beta DGlcNAc(1-6)\beta DGlcNAc-O-(CH_2)_5CONHNH_2$ was conjugated with rIL-2 using Procedure A as described in the section entitled "Procedures for adding Mono- or oligosaccharides to rIL-2". The carbohydrate (8.80 mg) was dissolved in 1 mL of DMF and then coupled to 6.0 mg of rIL-2. The ratio of oligosaccharide to rIL-2 was 1.5 to 1 by weight. The weight of the HPLC recovered protein was 2.28 mg. $\beta DGlcNAc(1-6)\beta DGlcNAc-O-(CH_2)_5CONHNH_2$ conjugated with rIL-2 was tested for its solubility, its ability to enhance NK cell activity, generate LAK cell activity, and stimulate lymphocyte proliferation.

Results:

Solubility: readily soluble in an aqueous solution

| NK enhancing activity: | 18% |
|---|---|
| LAK generating activity: | 9% |
| Ability to stimulate the proliferation of lymphocytes: | 3% |

EXAMPLE 7

Synthesis of $\beta DGalNAc(1-4)\beta DGal(1-4)\beta DGlc-O-(CH_2)_5CONHNH_2$ (Asialo-GM2 Acylhydrazide) and the Properties of rIL-2 Conjugated with it The methyl ester, $\beta DGalNAc(1-4)\beta DGal(1-4)\beta DGlc-O-(CH_2)_5COOCH_3$ (asialo-GM2 tether methyl ester) was made according to the reported procedure of Sabesan et al., Can. J. Chem., 62:1034 (1984), except the product was made as the 5-methoxycarbonylpentyl glycoside instead of the 8-methoxycaronyloctyl glycoside. This methyl ester (200 mg) was refluxed with 7 mL of hydrazine and 20 mL of methanol for 2 h, evaporated to dryness and purified as described in Example 1. Yield 164 mg.

Conjugation of Asialo-GM2 tether-acylhydrazide to rIL-2

Procedure A:

Asialo-GM2 tether-acylhydrazide (8.55 mg) was dissolved in DMF (800 uL) and the solution was cooled to −20° C. 4 M hydrochloric acid in dioxane (13 uL) and a solution of t-butyl nitrite (2.4 uL) were added and the solution was stirred at −20° C. for 30 min. Sulfamic acid (0.49 mg in 10 μL of DMF) was added and the solution was cooled to −30° C. After 10 min, this was added to a solution of r-IL2 (5.8 mg) in sodium borate buffer (prepared as described in Procedure A). After 24 h the product was purified as described in the general procedure. Yield 2.37 mg.

$\beta DGalNAc(1-4)\beta DGal(1-4)\beta DGlc-O-(CH_2)_5CONHNH_2$ (asialo-GM2 tether-acylhydrazide) conjugated with rIL-2 was tested for its solubility, its ability to enhance NK cell activity, generate LAK cell activity, and stimulate lymphocyte proliferation. The ratio of oligosaccharide to rIL-2 was 1.5 to 1 by weight.

Results:

Solubility: readily soluble in an aqueous solution

| NK enhancing activity: | 103% |
|---|---|
| LAK generating activity: | 123% |
| Ability to stimulate the proliferation of lymphocytes: | 5% |

Procedure B:

The preparation was the same as above except the asialo-GM2 tether-acylhydrazide was dissolved in 800 μL of water and sodium nitrite was used instead of t-butyl nitrite. Also, the sulfamic acid solution was made in water. Yield 2.67 mg.

βDGalNAc(1-4)βDGal(1-4)βDGlc-O-(CH$_2$)$_5$CONHNH$_2$ (asialo-GM2 tether-acylhydrazide) conjugated with rIL-2 was tested for its solubility, its ability to enhance NK cell activity, generate LAK cell activity, and stimulate lymphocyte proliferation. The ratio of oligosaccharides to rIL-2 was 1.5 to 1 by weight.

Results:

Solubility: readily soluble in an aqueous solution.

| NK enhancing activity: | 76% |
|---|---|
| LAK generating activity: | 89% |
| Ability to stimulate the proliferation of lymphocytes: | 8% |

Preparation of Glycosylated rIL-2 to Contain Different Quantities of βDGalNAc(1-4)βDGal(1-4)βDGlc-O-(CH$_2$)$_5$CONHNH$_2$ (asialo-GM2 tether-acylhydrazide)

Batch 1 Procedure A:

The trisaccharide tether-acylhydrazide βDGalNAc(1-4)βDGal(1-4)βDGlc-O-(CH$_2$)$_5$CONHNH$_2$ (17 mg) (asialo-GM2 tether-acylhydrazide), synthesized as in Example 7 was converted to the acylazide in 1 mL of DMF as described in Example 7. Five tubes containing 5 mg each of rIL-2 in sodium borate buffer at pH 9.0 were prepared as described in Procedure A and stirred in an ice bath. Aliqouts consisting of 100 μL, 200 μL, 300 μL, and 400 μL of the acylazide solution were added to four vials containing 900 μL, 800 μL, 700 μL, and 600 μL, respectively, of DMF at −30° C. The solutions were gently shaken. Each of these solutions and a control solution of DMF only, was then added to one of the five rIL-2 solutions, respectively, and the resulting solutions were stirred in a cold room for 16 h. Final purification of the resulting glycosylated IL-2 preparations was carried out as described in the Procedure For Recovery and Purification Of Glycosylated rIL-2. The resulting samples of product were labeled 24-1, 24-2, 24-3, 24-4 and 24-5, respectively. The rIL-2 in sample 24-1 was not reacted with any hydrazide solution while samples 24-2 through 24-5 were reacted as described above with increased amounts of βDGalNAc(1-4)βDGal(1-4)βDGlc-O-(CH$_2$)$_5$CONHNH$_2$ (17 mg) (asialo-GM2 tether-acylhydrazide), i.e., ratios of oligosaccharides to rIL-2 of 0.3 to 1, 0.7 to 1, 1.1 to 1 and 1.4 to 1, respectively.

Each preparation was tested for its solubility, its ability to enhance NK cell activity, generate LAK cell activity, and stimulate lymphocyte proliferation.

Results:

Solubility: Sample 24-1 was not easily dissolved. All the other samples of this Example were readily soluble in an aqueous solution. Samples 24-4 and 24-5 were more readily dissolved than samples 24-2 and 24-3.

| Control Sample 24-1 | |
|---|---|
| NK enhancing activity: | 62% |
| LAK generating activity: | 88% |
| Ability to stimulate the proliferation of lymphocytes: | 57% |
| No carbohydrate | |
| Sample 24-2 | |
| NK enhancing activity: | 82% |
| LAK generating activity: | 71% |
| Ability to stimulate the proliferation of lymphocytes: | 41% |
| ratio of oligosaccharide:rIL-2 | 0.3:1 |
| Sample 24-3 | |
| NK enhancing activity: | 78% |
| LAK generating activity: | 74% |
| Ability to stimulate the proliferation of lymphocytes: | 24% |
| ratio of oligosaccharide:rIL-2 | 0.7:1 |
| Sample 24-4 | |
| NK enhancing activity: | 50% |
| LAK generating activity: | 50% |
| Ability to stimulate the proliferation of lymphocytes: | 20% |
| ratio of oligosaccharide:rIL-2 | 1.0:1 |
| Sample 24-5 | |
| NK enhancing activity: | 36% |
| LAK generating activity: | 34% |
| Ability to stimulate the proliferation of lymphocytes: | 17% |
| ratio of oligosaccharide:rIL-2 | 1.4:1 |

Batch 2 Procedure A:

The trisaccharide tether-acylhydrazide βDGalNAc(1-4)βDGal(1-4)βDGlc-O-(CH$_2$)$_5$CONHNH$_2$ (asialo-GM2 tetheracylhydrazide) (102 mg) was dissolved in 3 mL of DMF. The solution was cooled to −20° C. Hydrochloric acid (4 M) in 1,4-dioxane (156 uL) and 0.71 M t-butyl nitrite solution in DMF (300 uL) were added and the solution was stirred at −20° C. for 30 min. Sulfamic acid solution (120 μL, 5 M) was added at this time and the solution was cooled to −30° C. After 10 min, 300 μL, 400 μL, 500 μL, 750 μL and 1000 μL portions of this acylazide solution were added, respectively, to five different vials containing 700 μL, 600 μL, 500 μL, 250 μL, and no DMF at −30° C. Five tubes containing 6 mg of rIL-2 in 5 mL of sodium borate buffer (pH 9.0) were cooled in an ice bath. The DMF solution from the five vials were added, respectively to the five rIL-2 solution and then stirred in cold room for 16 h. The resulting samples were labeled 30-1, 30-2, 30-3, 30-4, and 30-5, respectively. Sample 30-1 corresponded to the sample wherein rIL-2 was reacted with 300 μL of hydrazide solution and the others with 400, 500, 750, and 100 μL, respectively. Each glycosylated rIL-2 sample was purified as described in the Procedure For Recovery and Purification Of Glycosylated rIL-2.

Each preparation was tested for its solubility, its ability to enhance NK cell activity, generate LAK cell activity, and stimulate lymphocyte proliferation. Sample 30-2 was tested for heat stability at 20° C. and 90° C. by circular dichroism spectroscopy. (FIG. 2)

Results:

All the samples of recovered glycosylated rIL-2 in this Example were readily soluble in an aqueous solution.

| Control Sample 30-1 | |
|---|---|
| NK enhancing activity: | 87% |
| LAK generating activity: | 98% |
| Ability to stimulate the proliferation of lymphocytes: | 8% |
| ratio of oligosaccharide:rIL-2 | 1.4:1 |
| Sample 30-2 | |
| NK enhancing activity: | 56% |

| | |
|---|---|
| LAK generating activity: | 73% |
| Ability to stimulate the proliferation of lymphocytes: | 6% |
| ratio of oligosaccharide:rIL-2 | 1.9:1 |
| Sample 30-3 | |
| NK enhancing activity: | 31% |
| LAK generating activity: | 35% |
| Ability to stimulate the proliferation of lymphocytes: | 6% |
| ratio of oligosaccharide:rIL-2 | 2.4:1 |
| Sample 30-4 | |
| NK enhancing activity: | 17% |
| LAK generating activity: | 7% |
| Ability to stimulate the proliferation of lymphocytes: | 2% |
| ratio of oligosaccharide:rIL-2 | 3.4:1 |
| Sample 30-5 | |
| NK enhancing activity: | 22% |
| LAK generating activity: | 18% |
| Ability to stimulate the proliferation of lymphocytes: | 1% |
| ratio of oligosaccharide:rIL-2 | 4.7:1 |

Preparation of Differentially Glycosylated rIL-2 using Procedure B

βDGalNAc(1-4)βDGal(1-4)βDGlc-O-(CH$_2$)$_5$CONHNH$_2$ (asialo-GM2 tether-acylhydrazide) (46.5 mg) was dissolved in 9.3 mL of water and the solution was stirred in an ice bath. An aliquot (110 μL) of a solution of hydrochloric acid (4 M) in dioxane and 380 μL of sodium nitrite solution (51 mg of sodium nitrite dissolved in 1.029 ml of water) were added and the solution was stirred for 60 min. This resulting reaction mixture will be referred to as the asialo-GM2 tether-acylazide solution in the following text.

rIL-2 (22.0 mg) was dissolved in 20.3 mL of a buffer described in Procedure A and the pH of the solution was adjusted to 9.0 by the addition of 0.85 M potassium hydroxide. The total volume was adjusted to 22 mL with distilled water and 2 mL of this was transferred to each of eleven tubes and then cooled in ice bath. To the tubes were added 0, 100, 200, 300, 400, 800, 1000, 1200, 1400, 1600, 2000 μL of acylazide solution, respectively, and samples 1 through 11 were stirred in a cold room for 24 h. These were then purified as described in Procedure For Recovery and Purification of Glycosylated rIL-2.

Each preparation was tested for its solubility, its ability to enhance NK cell activity, generate LAK cell activity, and stimulate lymphocyte proliferation.

Results:

Solubility: All the samples of glycosylated rIL-2 was readily soluble in an aqueous solution.

| | |
|---|---|
| Control Sample 1 | |
| NK enhancing activity: | 53% |
| LAK generating activity: | 60% |
| Ability to stimulate the proliferation of lymphocytes: | 100% |
| No carbohydrate | |
| Sample 2 | |
| NK enhancing activity: | 111% |
| LAK generating activity: | 122% |
| Ability to stimulate the proliferation of lymphocytes: | 84% |
| ratio of oligosaccharide:rIL-2 | 0.2:1 |
| Sample 3 | |
| NK enhancing activity: | 129% |
| LAK generating activity: | 100% |
| Ability to stimulate the proliferation of lymphocytes: | 98% |
| ratio of oligosaccharide:rIL-2 | 0.5:1 |
| Sample 4 | |
| NK enhancing activity: | 156% |
| LAK generating activity: | 192% |
| Ability to stimulate the proliferation of lymphocytes: | 75% |
| ratio of oligosaccharide:rIL-2 | 0.7:1 |
| Sample 5 | |
| NK enhancing activity: | 204% |
| LAK generating activity: | 200% |
| Ability to stimulate the proliferation of lymphocytes: | 67% |
| ratio of oligosaccharide:rIL-2 | 1.0:1 |
| Sample 6 | |
| NK enhancing activity: | 72% |
| LAK generating activity: | 87% |
| Ability to stimulate the proliferation of lymphocytes: | 28% |
| ratio of oligosaccharide:rIL-2 | 1.9:1 |
| Sample 7 | |
| NK enhancing activity: | 112% |
| LAK generating activity: | 93% |
| Ability to stimulate the proliferation of lymphocytes: | 28% |
| ratio of oligosaccharide:rIL-2 | 2.4:1 |
| Sample 8 | |
| NK enhancing activity: | 100% |
| LAK generating activity: | 114% |
| Ability to stimulate the proliferation of lymphocytes: | 20% |
| ratio of oligosaccharide:rIL-2 | 2.9:1 |
| Sample 9 | |
| NK enhancing activity: | 109% |
| LAK generating activity: | 108% |
| Ability to stimulate the proliferation of lymphocytes: | 22% |
| ratio of oligosaccharide:rIL-2 | 3.3:1 |
| Sample 10 | |
| NK enhancing activity: | 76% |
| LAK generating activity: | 100% |
| Ability to stimulate the proliferation of lymphocytes: | 21% |
| ratio of oligosaccharide:rIL-2 | 3.8:1 |
| Sample 11 | |
| NK enhancing activity: | 65% |
| LAK generating activity: | 49% |
| Ability to stimulate the proliferation of lymphocytes: | 16% |
| ratio of oligosaccharide:rIL-2 | 4.8:1 |

EXAMPLE 8

Synthesis of βDGal(1-4)βDGlcNAc(1-6)βDGlcNAc-O-(CH$_2$)$_5$CONHNH$_2$ and the Properties of rIL-2 Conjugated with it A solution of βDGlcNAc(1-6)βDGlcNAc-O-(CH$_2$)$_5$CONHNH$_2$ (Example 6, 97 mg), UDP-Galactose (100 mg) and galactosyltransferase (10 U) were incubated at 37° C. in 10 mL of a buffer containing manganese chloride (1 mM), sodium cacodylate (pH 7.0, 1 mM) and bovine serum albumin for 4 h. The reaction was purified as described in Example 5. Yield 43.3 mg.

βDGal(1-4)βDGlcNAc(1-6)βDGlcNAc-O-(CH$_2$)$_5$CONHNH$_2$ was conjugated with rIL-2 using Procedure A as described in the section entitled "Procedures for adding Mono- or oligosaccharides to rIL-2"; 40.3 mg of the carbohydrate was coupled to 11.4 mg of r-IL2. The ratio of oligosaccharide to rIL-2 by weight was 3.5 to 1. The weight of the HPLC purified product was 4.2 mg. βDGal(1-4)βDGlcNAc(1-6)βDGlcNAc- O-(CH$_2$)$_5$CONHNH$_2$ conjugated with rIL-2 was tested for its solubility, its ability to enhance NK cell activity, generate LAK cell activity, and stimulate lymphocyte proliferation.

Results:

Solubility: significantly more soluble in an aqueous solution at a physiological pH than native rIL-2.

| | |
|---|---|
| NK enhancing activity: | 121% |
| LAK generating activity: | 100% |
| Ability to stimulate the proliferation of lymphocytes: | 25% |

EXAMPLE 9

Synthesis of
βDGal(1-3)βDGalNAc(1-4)βDGal(1-4)βDGlc-O-(CH$_2$)$_5$CONHNH$_2$ (Asialo-GM1 Tether-Acylhydrazide) and the Properties of rIL-2 Conjugated with it The methyl ester, βDGal(1-3)βDGalNAc(1-4)βD-Gal(1-4)βDGlc-O-(CH$_2$)$_5$COOCH$_3$ was made according to the published procedure of Sabesan et al., Can. J. Chem., 2:1034 (1984) except for the use of 5-methoxycarbonylpentanol instead of 8-methoxycarbonyloctanol. The methyl ester (721 mg) was then refluxed with 10 mL of hydrazine and 30 mL of methanol for 3 h. The product was purified as described in Example 1. Yield 625 mg.

Asialo-GM1 tether-acylhydrazide (21.1 mg) was reacted with 1.0 mL of DMF (Procedure A) containing 27 μL of hydrochloric acid in dioxane (3.9 M) and t-butyl nitrite (4.5 μL) followed by reacting with sulfamic acid (0.97 mg in 20 μL of DMF) and rIL-2 (5.0 mg) solution as described in Procedure A. The ratio of oligosaccharide to rIL-2 by weight was 4.2 to 1. The reaction mixture was dialyzed against deionized water and the product was lyophilized (0.756 mg).

βDGal(1-3)βDGalNAc(1-4)βDGal(1-4)βDGlc-O-(CH$_2$)$_5$CONHNH$_2$ conjugated with rIL-2 was tested for its solubility, its ability to enhance NK cell activity, generate LAK cell activity, and stimulate lymphocyte proliferation.

Results:

Solubility: significantly more soluble in an aqueous solution at a physiological pH than native rIL-2.

| | |
|---|---|
| NK enhancing activity: | 21% |
| LAK generating activity: | 15% |
| Ability to stimulate the proliferation of lymphocytes: | 1% |

EXAMPLE 10

Sialylation of Glycosylated rIL-2 rIL-2 (5.8 mg) was glycosylated according to Procedure A with 40 mg of the trisaccharide of Example 8 which contained about 40% sodium cacodylate. After purification by means of HPLC, about 1.5 mg of the glycosylated rIL-2 was obtained. The ratio of oligosaccharide to rIL-2 by weight was 6.9 to 1. This was then sialylated as follows.

Figure 3:
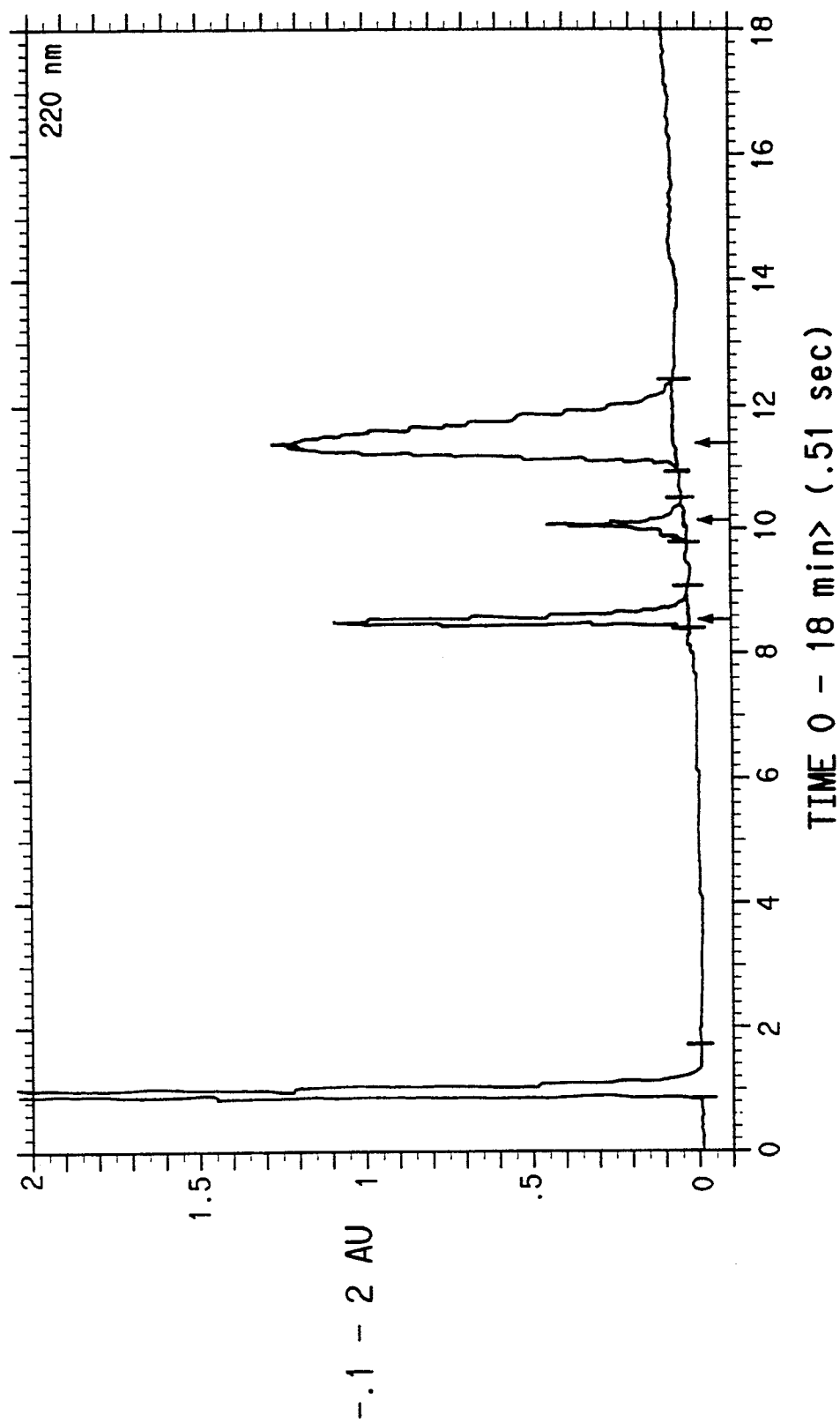
FIG. 3 shows the HPLC elution profile of the sialylated βDGal(1-4)βDGlcNAc(1-6)βDGlcNAc-O-(CH$_2$)$_5$CONH-rIL-2 produced in Example 10.

The rIL-2 glycosylated with the trisaccharide βDGal(1-4)βDGalNAc(1-6)βDGlc-O-(CH$_2$)$_5$CONHNH$_2$ (1.5 mg) was dissolved in a buffer (pH 6.0) containing 50 mM sodium cacodylate, 0.5% glycerol, bovine serum albumin (1 mg) and cytidinemonophosphate-N-acetylneuraminic acid (10.0 mg). Gal β1,4GlcNAcβ2,6-sialyltransferase (E.C. 2.4.99.5, 100 mU) was added and incubated at 37° C. for 5.5 h. The product was purified from the reaction mixture by HPLC using a reverse phase column as described above and as shown in FIG. 3). BSA eluted at 8.54 minutes while the sialylated rIL-2 eluted at 11.43 minutes. The product eluted about 0.51 min earlier than the starting material. The solution was lyophilized and stored at −78° C. in 0.3 M glucose solution until tested.

Sialylated βDGal(1-4)βDGlcNAc(1-6)βDGlcNAc conjugated with rIL-2 was tested for its solubility, its ability to enhance NK cell activity, generate LAK cell activity, and stimulate lymphocyte proliferation.

Results:

Solubility: significantly more soluble in an aqueous solution at a physiological pH than native rIL-2.

| | |
|---|---|
| NK enhancing activity: | 63% |
| LAK generating activity: | 71% |
| Ability to stimulate the proliferation of lymphocytes: | 12% |

EXAMPLE 11

Synthesis of
βDGal(1-4)βDGlcNAc(1-6){βDGal(1-4)βDGlcNAc(1-4)}βDGal(1-4)βDGlc-O(CH$_2$)$_5$CONHNH$_2$ and the properties of rIL-2 conjugated with it The synthesis of the oligosaccharide was accomplished starting from the diol (11a, Scheme 2) 5-methoxy-carbonylpentyl-2,3,6-tri-O-acetyl-4-O-(2,3-di-O-actyl-β-D-galactopyranosyl)-β-D-glucopyranoside (11a, Scheme 2) which was prepared according to the procedure of Sabesan et al., Can. J. Chem., 62:1034 (1984).

Scheme 2

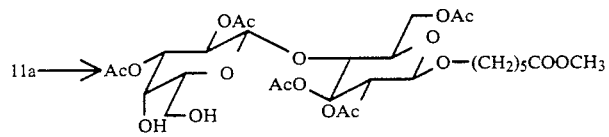

Scheme 2

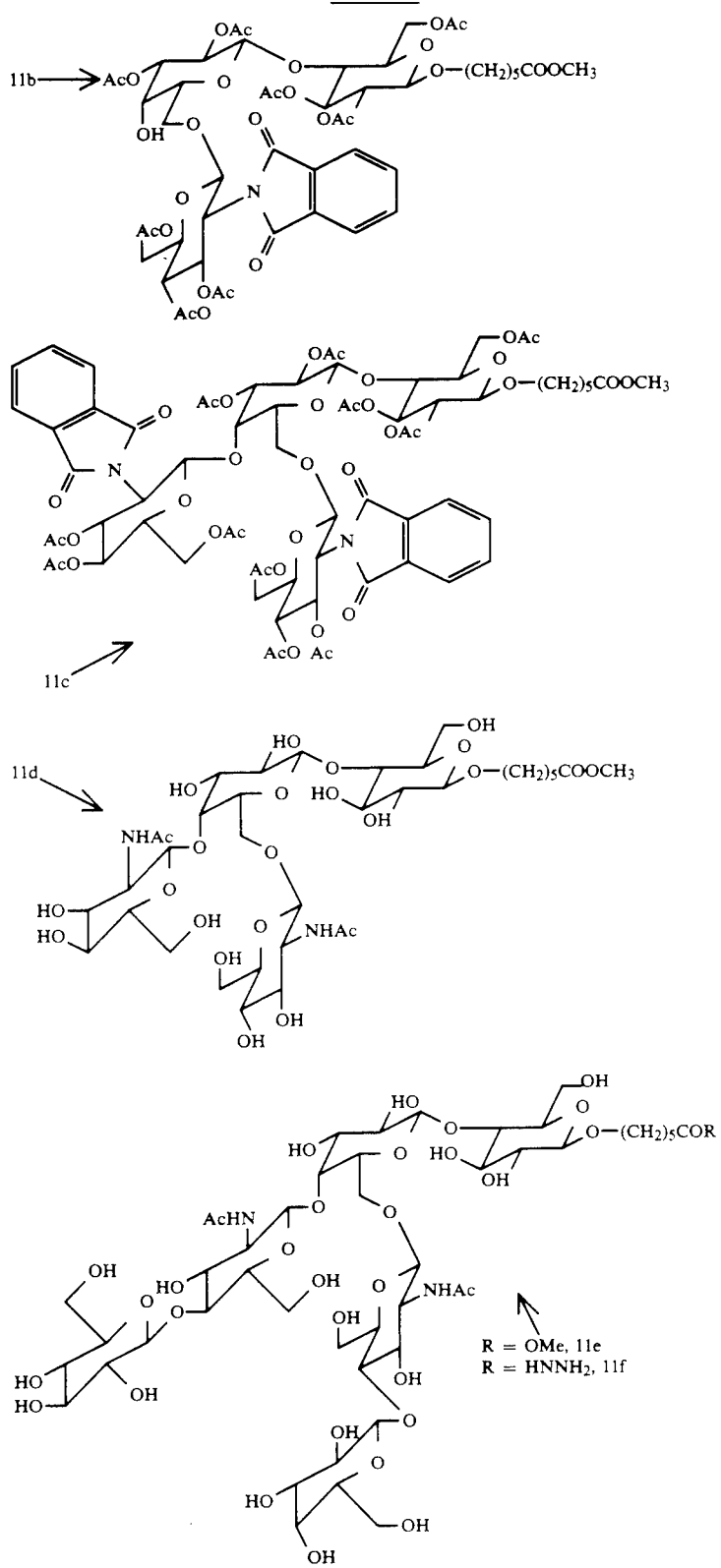

R = OMe, 11e
R = HNNH₂, 11f

The alcohol 11a (3.20 g, 4.7 mmol) was dissolved in anhydrous nitromethane (100 mL) containing silver triflate (2.66 g, 10.36 mmol), collidine (1.2 mL, 8.95 mmol) and 4A molecular sieves. The mixture was kept under a dry nitrogen atmosphere and cooled to −28° C. 2-Deoxy-2-phthalimido-3,4,6-tri-O-acetyl-β-D-glucopyranosyl bromide (5.20 g, 10.36 mmol) was added and the mixture was stirred at this temperature for 6 h. The reaction mixture was diluted with dichloromethane (100 mL) and filtered over a bed of diatomaceous earth. The filtrate was washed with ice cold 0.5 M hydrochloric acid, water and saturated sodium bicarbonate solution. The organic layer was dried over anhydrous magnesium sulfate and evaporated to a dry residue. The major product was purified by chromatography on a column of silica gel using ethyl acetate-hexane-acetonitrile (8:9:2) as eluant Yield 3.94 g. $^1$H nmr confirmed the product to be the trisaccharide 11b. (Scheme 2)

The trisaccharide 11b (1.0 g) was again glycosylated with 2-deoxy-2-phthalimido-3,4,6-tri-O-acetyl-β-D-glucopyranosyl bromide (682 mg) in the presence of silver triflate (352 mg) and collidine (108 μL) as described above at room temperature for 16 h. A second batch of the bromide (682 mg), silver triflate (352 mg) and collidine (108 μL) was added and the reaction was continued at room temperature for 24 h. The reaction mixture was then worked up as described above and the product 11c (Scheme 2) was purified by silical gel chromatography (ethyl acetate-hexane-ethanol = 10:10:1 was used as column eluant) Yield 661 mg. The structure of 11c was confirmed by $^1$H nmr.

Compound 11c (641 mg) was dissolved in 15 mL of anhydrous methanol containing 200 μL of 0.5 M sodium methoxide solution and stirred under nitrogen for 16 h. The solution was then neutralized with H+ resin, filtered and evaporated to a dry residue (427 mg), which was redissolved in anhydrous methanol containing anhydrous hydrazine (130 μL) and refluxed for 24 h. The reaction mixture was then evaporated to dryness and dissolved in a 1:1 mixture of pyridine-acetic anhydride (20 mL) containing 10 mg of N,N-dimethylaminopyridine. After 24 h at room temperature, the reaction mixture was poured over ice and extracted with dichloromethane. The organic layer was washed with ice cold 1 M hydrochloric acid, water and saturated sodium bicarbonate solution, then dried over magnesium sulfate and evaporated to a dry residue. The product was purified on a column of silica gel using ethyl acetate-hexane-acetonitrileethanol (10:10:5:1) as eluant. The yield was 284 mg.

The above product (274 mg) was dissolved in anhydrous methanol (10 mL) containing 105 μL of 0.5 M sodium methoxide and stirred at room temperature for 3 h. The solution was then neutralized with acid resin, filtered and evaporated to a dry residue (170 mg). The structure of this product was confirmed as 11d (Scheme 2) by $^1$H nmr. Compound 11d (68 mg) was dissolved in a 100 mM sodium phosphate buffer (10.0 mL, pH 7.2) containing manganese chloride (100 mmol), bovine serum albumin (4.0 mg), uridinediphosphogalactose (200 mg, UDP-Galactose,Sigma Chemical Co. St. Louis, MO) and galactosyltransferase (EC.2.4.1.22, 25 U, Sigma Chemical Co. St. Louis, MO). The solution was incubated at 37° C. for 3 h. The product 11e from this mixture was purified as described in Example 5. The yield was 74 mg.

Compound 11e (64 mg) was refluxed in methanolhydrazine (5:2) mixture (7 mL) for 4 h. The solution was evaporated to dryness, redissolved in 5 mL of deionized water and applied on a column of Bio gel p2 (Biorad, 500 mL), equilibrated and eluted with water. The fractions containing the products were pooled and lyophilized. The yield was 55.3 mg. The structure of this product was established as 11f based on $^1$H nmr.

Conjugation of 11f to rIL-2

To a solution of compound 11f (24.0 mg) in water (Procedure B) (1.6 mL), 4 M hydrochloric acid in dioxane (26 μL) and sodium nitrite (50 μL of a stock solution containing 51.0 mg of sodium nitrite in 1 mL water) were added and the solution was stirred at 4° C. for 30 min. rIL-2 (7.0 mg) was suspended in 4 mL of sodium boratepotassium bicarbonate buffer (4 mL, pH 9.0) containing 500 μL of 10% sodium dodecylsulfate and the solution was kept in an ice bath. The solution containing 11f was then added and stirred at 4° C. for 24 h and then purified by HPLC as described in Procedure A. The ratio of oligosaccharide to rIL-2 was 3.4 to 1 by weight. Yield 5.08 mg.

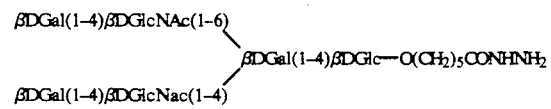

βDGal(1-4)βDGlcNAc(1-6)
βDGal(1-4)βDGlc—O(CH$_2$)$_5$CONHNH$_2$
βDGal(1-4)βDGlcNac(1-4)

conjugated with rIL-2 was tested for its solubility, its ability to enhance NK cell activity, generate LAK cell activity, and stimulate lymphocyte proliferation.

Results:

Solubility: significantly more soluble in an aqueous solution at a physiological pH than native rIL-2.

| | |
|---|---|
| NK enhancing activity: | 63% |
| LAK generating activity: | 91% |
| Ability to stimulate the proliferation of lymphocytes: | 52% |

What is claimed is:

1. A composition of matter comprising a lysine glycosylated rIL-21 wherein a carbohydrate-tether conjugate is covalently linked to an amino group of at least one lysine of the rIL-2 and wherein said lysine glycosylated rIL-2 demonstrates reduced T-cell stimulating activity as compared with unglycosylated rIL-2.

2. The composition of matter of claim 1 wherein the carbohydrate is selected from the group consisting of monosaccharides and oligosaccharides.

3. The composition of matter of claim 2 wherein the oligosaccharide comprises up to six monosaccharide residues.

4. The composition of matter of claim 1 wherein the tether comprises a linear ω-carbonylalkoxy group of the general structure $-O-(CH_2)_nCO-$ where n is in the range from about 4 to about 11.

5. The composition of matter of claim 2 wherein the monosaccharide is βDGal or βDGlcNAc.

6. The composition of matter of claim 3 wherein the oligosaccharide is selected from the group consisting of:

βDGal(1-3)βDGalNAc;
βDGal(1-3)βDGlcNAc;
βDGal(1-4)βDGlcNAc;
βDGlcNAc(1-6)βDGlcNAc;
βDGalNAc(1-4)βDGal(1-4)βDGlc;
βDGal(1-4)βDGlcNAc(1-6)βDGlcNAc;
βDGal(1-3)βDGalNAc(1-4)βDGal(1-4)βDGlc;

and

βDGal(1-4)βDGlcNAc(1-6)
βDGal(1-4)βDGlc.
βDGal(1-4)βDGlcNAc(1-4)

* * * * *